US010085860B2

(12) United States Patent
Steckel et al.

(10) Patent No.: US 10,085,860 B2
(45) Date of Patent: Oct. 2, 2018

(54) MAGNESIUM-BASED ABSORBABLE IMPLANTS

(71) Applicant: Zorion Medical, Inc., Zionsville, IN (US)

(72) Inventors: Mark Steckel, Glasgow (GB); Ioannis O. Pandelidis, Sharon, MA (US)

(73) Assignee: ZORIAN MEDICAL, INC., Zionsville, IN (US)

( * ) Notice: Subject to any disclaimer, the term of this patent is extended or adjusted under 35 U.S.C. 154(b) by 382 days.

(21) Appl. No.: 14/624,138

(22) Filed: Feb. 17, 2015

(65) Prior Publication Data

US 2015/0157478 A1 Jun. 11, 2015

Related U.S. Application Data

(62) Division of application No. 13/309,271, filed on Dec. 1, 2011, now Pat. No. 8,986,369.

(60) Provisional application No. 61/458,706, filed on Dec. 1, 2010, provisional application No. 61/460,464, filed on Jan. 4, 2011.

(51) Int. Cl.
| | | |
|---|---|---|
| A61F 2/06 | (2013.01) |
| A61F 2/86 | (2013.01) |
| A61L 27/04 | (2006.01) |
| A61L 27/58 | (2006.01) |
| A61L 31/02 | (2006.01) |
| A61L 31/14 | (2006.01) |
| C25F 3/18 | (2006.01) |
| C25F 3/24 | (2006.01) |
| A61B 17/122 | (2006.01) |
| A61B 17/80 | (2006.01) |
| A61B 17/86 | (2006.01) |
| A61B 17/00 | (2006.01) |
| A61B 17/04 | (2006.01) |

(52) U.S. Cl.
CPC .............. *A61F 2/86* (2013.01); *A61L 27/04* (2013.01); *A61L 27/58* (2013.01); *A61L 31/022* (2013.01); *A61L 31/148* (2013.01); *C25F 3/18* (2013.01); *C25F 3/24* (2013.01); *A61B 17/122* (2013.01); *A61B 17/80* (2013.01); *A61B 17/866* (2013.01); *A61B 2017/00004* (2013.01); *A61B 2017/0417* (2013.01); *A61F 2210/0004* (2013.01); *A61F 2210/0076* (2013.01)

(58) Field of Classification Search
CPC ... A61F 2/06; A61F 2/86; A61B 17/80; A61B 17/122; A61B 17/86; A61B 2017/0417; A61B 2017/00004
See application file for complete search history.

(56) References Cited

U.S. PATENT DOCUMENTS

2007/0208409 A1* 9/2007 Quigley .................... A61F 2/07
623/1.13
2009/0171452 A1* 7/2009 Yamamoto ............ A61L 31/022
623/1.38

* cited by examiner

*Primary Examiner* — Victor Nguyen
(74) *Attorney, Agent, or Firm* — Quarles & Brady LLP

(57) ABSTRACT

An implantable tissue filler including a particulate material suspended in a carrier, the particulate material having more than about 70% by weight magnesium and about 2-20% by weight lithium, wherein the particulate material is substantially free of rare earth metals.

29 Claims, 6 Drawing Sheets

MAGNESIUM-BASED ABSORBABLE IMPLANTS

CROSS-REFERENCE TO RELATED APPLICATIONS

This application is a divisional of U.S. patent application Ser. No. 13/309,271 filed Dec. 1, 2011, and entitled "Magnesium-Based Absorbable Implants," which in turn claims priority to, and the benefit of U.S. Provisional Patent Application Ser. No. 61/458,706, filed Dec. 1, 2010 and U.S. Provisional Patent Application Ser. No. 61/460,464, filed Jan. 4, 2011. The disclosures of each of these applications are incorporated by reference herein in their entireties.

TECHNICAL FIELD

This application relates generally to implants, and more specifically to bioabsorbable intraluminal implants.

BACKGROUND OF THE INVENTION

The statements in this section merely provide background information related to the present disclosure and should not be construed as constituting prior art.

The field of coronary angioplasty and stenting has made significant progress in treatment of coronary heart disease through at least three generations of product technology. However, each generational advancement has been accompanied by new challenges. Balloon angioplasty therapy improved acute luminal flow, but vessel recoil and remodeling resulted in high restenosis rates. Bare metal stenting eliminated vessel recoil and minimized abrupt closure events, but restenosis rates were still high due to stent mechanical injury and resulting smooth muscle cell (SMC) migration and proliferation into the lumen.

The current standard of care for treating most de novo coronary lesions is the implantation of a permanent implant known as a drug eluting stent ("DES"). The DES is a third generation angioplasty device for treating coronary stenosis, with significantly lower re-intervention rates than either bare metal stents or balloon angioplasty. This generation of technology is a permanent implant, typically including a high strength and high radio-opacity metal such as cobalt chrome or platinum-enriched stainless steel, coated with a formulation of an anti-proliferative drug in a controlled release polymer.

The next generation of technology is a fully absorbable DES, i.e., the entire mechanical scaffolding (stent) and the drug formulation is broken down in the body and absorbed. The working hypothesis is that any permanent foreign body at the site can prolong inflammation and delay healing and restoration to its native state.

Drug eluting stents cut the retreatment rate significantly by addressing the SMC proliferation with a pharmaceutical agent, but also was accompanied by a "new" complication, late stent thrombosis (LST) and the accompanying extended use of anti-coagulants. LST is believed to result from this delayed healing, and is associated with mortality rates of 30-50%. The apparent factors driving LST appear to be the loss of vaso-motion and delayed healing of a functional endothelium.

Fully absorbable DES have been based on either absorbable polymer technology, such as the well-known PLGA family, or on reactive metals such as magnesium, that readily convert to metallic oxides and organo-metallics in vivo. The magnesium-based approach offers advantages in expandability and radial strength relative to the polymer approaches; however the alloys and manufacturing methods previously used have resulted in stent designs of insufficient ductility to withstand deployment and normal deformations within human arteries.

In particular, attempts to use magnesium and its alloys as a temporary implant biomaterial in cardiovascular stents have been hindered by poor control over the rate and uniformity of the metal's degradation (metallic corrosion rate), fragmentation, and absorption processes in local tissue. Previous attempts at controlling degradation or corrosion rate have focused on alloying with rare earth and other heavy metal elements of unknown biocompatibility, yielding slower corrosion rates but unproven benefits in clinical performance.

Although these approaches have merit for non-medical applications such as commercial or aerospace castings, they are sub-optimal for an absorbable implant grade material that will eventually be fully metabolized by the host tissue, releasing alloying elements of unknown biocompatibility.

It is known that certain metallic impurities in magnesium alloys can rapidly increase its corrosion rate in the presence of physiologic fluids containing chlorides (saline). Most notably are metals such as Fe or Cu, which can form a second phase with dissimilar electronegativities to the magnesium alloy, creating a micro-galvanic cell with vastly increased corrosion rates at the interface. Accordingly, it is common practice in the industry to limit these impurities to low levels (Fe for example to less than 150 ppm), or to alloy with other elements that form complexes with any free Fe to minimize the potential of the micro-galvanic corrosion. However for an absorbable implant grade alloy, these additional elements pose new toxicity concerns.

Furthermore, conventional approaches for corrosion control of magnesium alloys have focused solely on preventing the initial mechanical failure of the given article by retarding the degradation process either by a surface passivation layer, or by changing the local corrosion potential of the alloy. Consideration has not been given to controlling the process of fragmentation, disintegration and absorption following initial mechanical failure. For many implant applications, the timing and nature of the full degradation process, starting with the as-implanted metal article to the final clearance of the alloy mass and its degradants from the anatomical site, is critical for the performance of the medical device.

One such implant application is absorbable metal stents for vascular or luminal scaffolding, such as stents for treatment of coronary artery disease. In this application, the stents provide a temporary scaffolding through the healing process related to the local injury caused by the high pressure angioplasty balloon used to open the stenosed or partially blocked artery. The metal scaffold is required only for a period of days to weeks to prevent abrupt closure of the vessel from spasm, minimize elastic recoil, and as a substrate to deliver a controlled release drug-polymer formulation to the site of injury. After this period, any remnant of the alloy or its degradants is a liability, since it can act as a foreign body prolonging an inflammatory response and delay healing. Furthermore, if the stent remnants remain present in the lumen in solid form through the period of extracellular matrix deposition and scar formation, then the stent remnants themselves become a source of lumen obstruction and participate in a new form of restenosis unknown to conventional permanent stents.

SUMMARY OF THE INVENTION

In accordance with one embodiment of the present invention, an implantable tissue filler is provided comprising a particulate material suspended in a carrier, wherein the particulate material comprises more than about 70% by weight magnesium and about 2-20% by weight lithium. In accordance with this embodiment, the particulate material is substantially free of rare earth metals.

In accordance with another embodiment of the present invention, a bioabsorbable implant is provided comprising an elongated metallic element comprising a core and at least two layers of alternating compositions selected from the group consisting of magnesium, iron, and alloys thereof disposed on the core, the elongated metallic element defining at least a portion of the bioabsorbable implant.

In accordance with still another embodiment of the present invention, a bioabsorbable implant is provided having at least three wires comprising magnesium and defining a cylindrical sheath surrounding and in intimate contact with at least one core wire comprising iron. In accordance with this embodiment, at least three wires and at least one core wire define at least a portion of the bioabsorbable implant.

In accordance with yet another embodiment of the present invention, a bioabsorbable implant is provided having a plurality of intertwined wires comprising magnesium and defining a strand, wherein (i) an Fe-rich layer formed by at least one of vapor, chemical and electro-deposition is defined on a surface of at least one of the wires, and (ii) the strand defines at least a portion of the bioabsorbable implant.

Still other objects and benefits of the invention will become apparent from the following written description along with the accompanying figures.

BRIEF DESCRIPTION OF THE DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Figure 1:
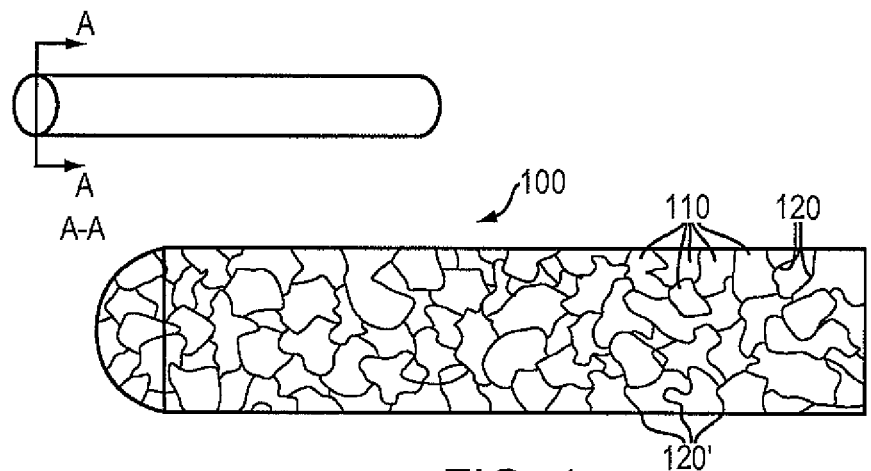
FIG. 1 is a schematic diagram of a segment of an elongated implant or sub-component such as a wire or pin with a conventional polycrystalline grain structure.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the specific methods and materials are now described. Moreover, the techniques employed or contemplated herein are standard methodologies well known to one of ordinary skill in the art and the materials, methods and examples are illustrative only and not intended to be limiting.

Embodiments of the invention may include a bioabsorbable implant that includes an elongated metallic element including an alloy including more than about 70% by weight magnesium and about 2-20% by weight lithium and being substantially free of rare earth metals. The elongated metallic element may define at least a portion of the bioabsorbable implant.

Mg—Li alloys with 70% magnesium and higher have superior mechanical properties in comparison to high lithium content alloys, especially alloys in which the lithium content exceeds 20%. Specifically, the stiffness, best represented by tensile and compressive modulus, of Mg—Li with a high lithium content is highly malleable, and hence insufficiently stiff and less suitable for load-bearing applications such as a coronary stent or an orthopedic implant than the compositions described herein.

The Mg—Li alloys described herein may be formed in a number of ways. In accordance with some embodiments of the invention, suitable Mg—Li alloys may be produced by an arc melting process. Preferably, due to the high reactivities of Mg and Li with air, the alloy is formed under partial vacuum and an inert gas environment such as argon, or under vacuum. The Mg and Li solid components are placed in a crucible. The arc melting process that reaches temperatures above 1000° C. creates a natural mixing of the Mg and Li elements without the need for any mechanical mixing device. In view of the high reactivity of Mg and Li, the use of an inert crucible, such as a boron nitride (BN) crucible is preferred, to avoid interaction of the crucible with Mg and Li. The crucible may either be made entirely of BN or may be formed of graphite with a BN coating or other suitable coatings.

The percentage weight ratio of Mg to Li results in the formation of the following phases of Mg—Li alloy:

Li 2.0-5.0% by weight, with the balance Mg, produces an alpha phase alloy;

Li 5.0-10.5% by weight, balance Mg, produces an alpha-beta phase alloy; and

Li greater than 10.5% by weight, balance Mg, produces a beta phase alloy.

The three alloy ranges differ in the relative proportions of 2 different crystallographic phases, i.e., pure alpha, pure beta, or a blend of both alpha and beta phases. The alpha phase has a hexagonal close-packed (hcp) crystal structure whereas the beta phase has a body-centered-cubic (bcc) crystal structure which is more ductile and malleable. The Li content of the alloy may be selected based on the desired properties for the intended application. In most implant applications, a maximum Li content of 20% by weight is contemplated to satisfy the mechanical strength requirements. For example, in stent applications a high radial force may be required to keep the arteries open acutely after the interventional procedure. Typical preferred mechanical properties may include an ultimate tensile strength, e.g., 100-160 MPa, with an ultimate elongation greater than 30%.

The mixture of solid Mg and solid Li is subsequently melted with a minimum temperature of 600° C. and cast into a mold to take the form of the mold; typically, a solid ingot is formed. An exemplary ingot shape is a solid rod with a diameter of 12 mm and a length of 6 to 8 cm. The solid rod may then be used as input material to a metal extruder that allows the rod to be transformed into an elongated rod with a smaller diameter and a longer length.

The resulting elongated rod may then be subjected to consecutive drawing operations passing through increasingly smaller diameter dies that reduce the diameter of the resulting wire with each drawing iteration. The wire is typically thermally annealed prior to each drawing step to restore ductility and improve the processability of the wire. The resulting final wire is produced in the as-hardened state, but may subsequently be fully or partially annealed to increase its ductility at the expense of mechanical strength.

The trade-off between ductility and mechanical strength is especially relevant in balloon expandable stents where both sufficient radial strength is desired to prevent the artery from prolapse, but ductility is also required to prevent breakage of struts during stent expansion. A preferred tensile strength for the Mg—Li alloys may be, e.g., 100-160 MPa. Ductility may be expressed in terms of elongation at break; a preferred elongation at break may be 30 to 50%, e.g., 9 to 45%.

In embodiments of the invention in which the Mg—Li alloys are employed in implantable devices, biocompatibility of the Mg—Li alloys is very important. Example 5 describes an in vivo study demonstrating the biocompatibility of an exemplary Mg—Li alloy of the invention.

In addition to Mg and Li, Mg—Li alloys in accordance with embodiments of the invention may include less than 10% of other elements such as strontium, calcium, zinc, and manganese. The addition of additional elements may provide improve certain characteristics of the material. For example, the addition of strontium and/or calcium may enhance corrosion resistance. Moreover, the addition of calcium may increase the mechanical strength of the alloy.

In various preferred embodiments, the Mg—Li alloy is substantially free of rare earth metals. Substantially free of rare earth metals, as used herein, means that the chemical composition of the alloy consists of less than 1.0% by weight of all rare earth elements combined, with the preferred value being less than 0.1% (by weight). Anything less than 0.1% is in the hundreds parts per million range, which is below the FDA threshold in safety profiles of individual impurities in drugs. At that level, rare earth metals also do not have a significant effect on corrosion properties. Rare earth and other high atomic number metals and their compounds are undesirable in implants because they are largely insoluble in physiologic fluids, which significantly delays absorption by local tissue.

The Mg—Li alloy of the invention may define a polycrystalline structure, a continuous single grain, or a columnar microstructure. In particular, referring to FIG. 1, a segment of an elongated implant 100 or sub-component such as a wire or pin with a conventional polycrystalline grain structure in cross-section A-A, has a plurality of grains 110 separated by grain boundaries 120. Mg—Li alloys are more easily formed in polycrystalline form, and polycrystalline material may be suitable for certain applications.

Figure 2:
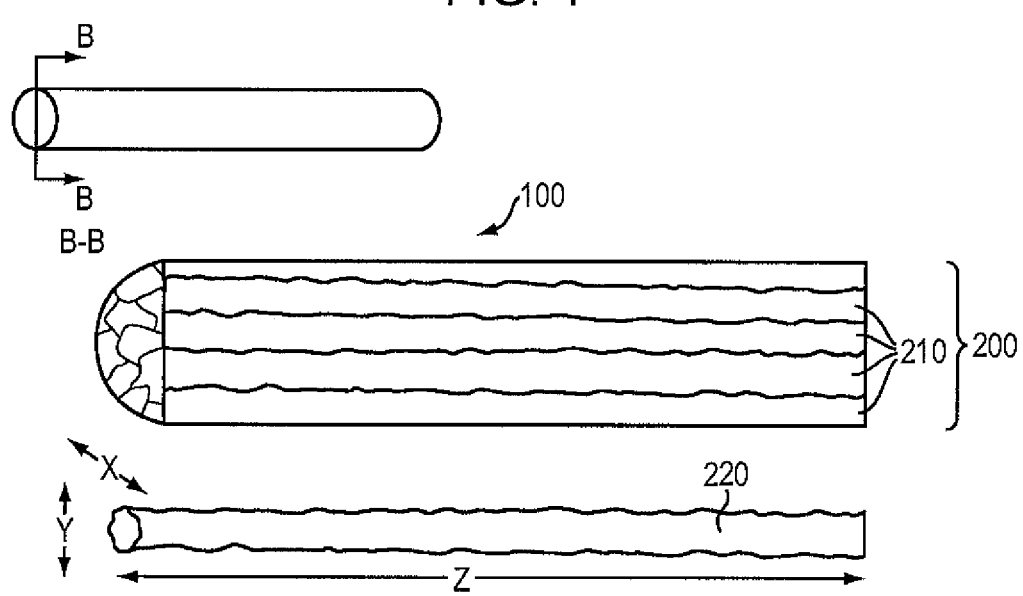
FIG. 2 is a schematic diagram of a segment of an elongated implant or sub-component processed by directional solidification that yields a plurality of columnar crystals in accordance with an embodiment of the invention.

In some applications, however, grain boundaries 120' that are aligned perpendicularly to the primary loading axis may be initiation points for premature failure due to accelerated corrosion or crack formation from fatigue. Accordingly, in some embodiments, a single crystal structure may be preferred, e.g., when certain mechanical strength, ductility, and/or material properties are desired. Thus, the crystal structure in accordance with some embodiments of the invention may be either single crystal (i.e., a continuous single grain) or columnar crystal structures (i.e., a columnar microstructure) that extend continuously for the length of the implant or implant sub-component. Referring to FIG. 2, a bioabsorbable implant may include an elongated metallic element or sub-component that may be formed by directional solidification that yields a columnar microstructure 200 plurality of columnar crystals 210 that extend essentially the full functional length of the implant 100. A single crystal structure 220 that is essentially without grain boundaries is shown for clarity, with dimensions of $z \gg x$, $z \gg y$.

If the metal defines a columnar microstructure 200, the columnar microstructure may include grains having an average grain length of preferably at least about 1 mm, and an average grain diameter of preferably less than about 0.2 mm. In some embodiments, the average grain length may be at least about 10 mm. The average grain diameter may be less than about 3 mm. The metal may include one or more grains having an aspect ratio of grain length to diameter of at least 10:1, preferably 100:1 or more.

To achieve such a controlled microstructure, the implant or implant sub-component may be processed from a melt by a process that controls the direction of solidification along its elongated axis. This may be achieved through controlled heat removal (under-cooling) at one end of the elongated structure so that crystal nucleation and propagation is driven down its length (z axis in FIG. 2), while crystal formation in the directions perpendicular to elongated axis are retarded by keeping those surfaces at an elevated temperature with insufficient under-cooling for nucleation. Additional mechanical forming processes can be practiced following directional solidification to achieve the final implant geometry, if the thermal treatments do not result in a re-crystallization that reverts the structure to polycrystalline.

A suitable process for forming at least a portion of an implant from a melt is the Ohno process. The Ohno process, typically used to form copper wires, is described in the literature. See, e.g.:

1. A. Ohno Casting of Near Net Shape Products, Edited by Y. Bahai, The Metallurgical Society (1988) 177;
2. X. Fan, Y. Cai Y, P. Wei, J. Li and H. Fu, Continuous casting technology of single crystal metals, Chinese Journal of Materials Research (June 1996) Vol. 10, No. 3, pp. 264-266;
3. Z. M. Zhang, T. Lu, C. J. Xu and X. F. Guo, Microstructure of binary Mg—Al eutectic alloy wires produced by the Ohno continuous casting process, ACTA Metall. Sin. (Engl. Lett.) Vol. 21, No. 4 (August 2008) pp. 275-281;
4. M. H. Kim, H. H. Jo and H. Y. Cho, Operating parameters for the continuous unidirectional solidification of the Al-1 wt. % Si Alloy drawn to fine wire, Metals and Materials, Vol. 6, No. 6 (2000) pp. 491-495; and
5. Y. J. Kim and S. Kou, An Experimental Study on Process Variables in Crystal Growth by Ohno Continuous Casting, Metallurgical Transactions A, Volume 19A (July 1988) pp. 1849.

Each of these references is incorporated by reference herein in its entirety.

In particular, the Ohno process is a continuous casting process that uses a heated mold, rather than a cooled mold. The mold is heated slightly above the melting point of the metal to be solidified. This has the result that no new grains can nucleate at the mold wall. Solidification is restricted to the contact area between the melt and the dummy rod or single crystal seed, which is withdrawn from the melt. The mold can be positioned either vertically upward, vertically downward, or horizontal. The melt stays in the mold even when the mold is not positioned vertically upward, as the die diameter is small, and grips or pinch rollers are needed to pull the wire out of the mold.

An advantage of the Ohno process is that it can be used for directional solidification or crystal growth, and ingots or crystals of unlimited length may be produced. The resulting material has a smooth surface and inner quality due to the fact that impurities are moved to the boundaries, resulting in a pure crystal. In addition superior mechanical properties are achieved due to the resulting directionally solidified microstructure.

One way to create a wire using the Ohno process is to utilize a crucible furnace with a melt level control, a heated mold with a small diameter channel, a cooling device to cool the wire after it exits the mold, and pinch rolls to pull the wire away from the mold.

Wire/bar drawing, a metalworking process known to those of skill in the art, allows for successive reductions in diameter of the bar/wire by pulling the wire/bar through successively smaller diameter dies. The successive reductions in diameter result in expansion of the length of the wire. The die is typically mounted on a draw bench and the end of the wire is placed in grips so that the rest of the wire may be pulled through the die. The process of drawing improves the mechanical properties of the wire due to work hardening.

In an exemplary process, eutectic Mg—Li wires of 5 mm in diameter with mirror-smooth surface may be continuously solidified with a casting speed 10 mm/min, a mold exit temperature of 450° C., a static pressure head of the melt of 5 mm, a flow rate of cooling water 30 L/h, and a mold-cooling water distance 20 mm. Under these casting conditions, the wires solidify just outside of the mold exit.

Figure 3:
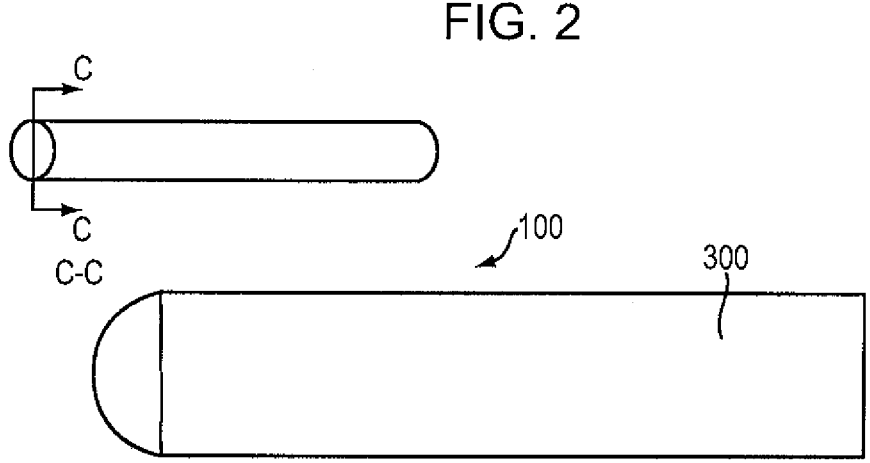
FIG. 3 is a schematic diagram of an elongated implant or sub-component formed of a single crystal that is essentially without grain boundaries in accordance with an embodiment of the invention.

Referring to FIG. 3, in some embodiments, a segment of an elongated implant or sub-component processed by directional solidification yields a single columnar crystal 300 that extends essentially the full functional length of the implant.

The elongated metallic element may define at least a portion of the bioabsorbable implant. The elongated metallic element may include a wire. The wire may have a diameter of less than about 0.2 mm. For intraluminal devices like stents, diameters above about 0.2 mm may create too much trauma to the vessel wall. On the other hand, in some embodiments such as ligating clips or suture anchors, diameters up to several mm may be preferred.

As discussed below, the elongated metallic element may include a wire formed into at least one discrete bioabsorbable expandable metal ring, or a wire formed into a bioabsorbable continuous helical sinusoid. The metal ring may be formed from welded wire forms or by laser micro-machining of metal tubing.

Figure 4:
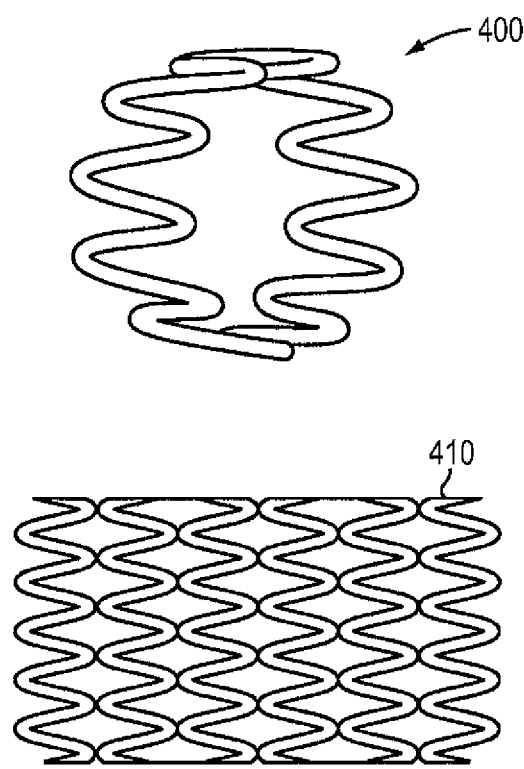
FIG. 4 is a schematic diagram of a segment of directionally solidified alloy formed into a sub-component of an implant, in accordance with an embodiment of the invention.

The bioabsorbable implant may be any one of various devices, such as an intraluminal device. Referring to FIG. 4, a segment of directionally solidified alloy may be formed into a sub-component of an implant, i.e., a ring element 400 of a balloon expandable coronary stent 410.

Figure 5:
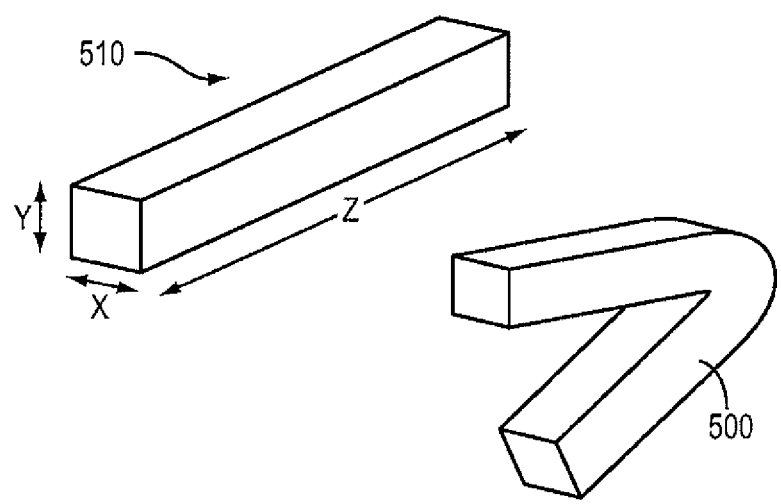
FIG. 5 is a schematic diagram of a segment of directionally solidified alloy formed into a ligating clip, in accordance with an embodiment of the invention.
Figure 5:
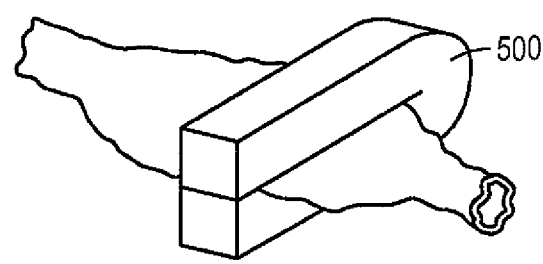

The bioabsorbable implant may also be a ligating clip or a ligating clip component. In particular, referring to FIG. 5, a segment of directionally solidified alloy may be formed into a ligating clip 500 for tubular anatomical structures. A ligating clip 500 may consist of a square wire 510. An exemplary ligating clip may be formed as follows. A magnesium-8.5% lithium alloy round wire of 1.4 mm in diameter may be formed by conventional drawing-annealing cycles from an extruded rod having an original diameter of 12 mm. These dimensions are adequate for providing mechanical integrity for a V shaped clip for ligating small hollow vessels (about 2 mm or less). Smaller or larger wires may be used, depending on the vessel size of the target indication. The 1.4 mm round wire may be formed into a square cross-section in 2 passes through a profile roller with an intermediate annealing operation. The square cross-section provides additional clamping area on a hollow vessel, in comparison to a round wire. A suitable profile roller is available from Roller Die+Forming based in Louisville, Ky. The square wire may be cut to a 14 mm length and bent into a "V" shape with an internal radius of about t 2 mm, so that stress on the hinge point is reduced. The clip may be sterilized and loaded into a re-usable clip applier for ligating small vessels. The high elongation of the Mg—Li alloy allows for the plastic deformation of the clip during closing around a hollow vessel, without fracturing at its hinge point.

Figure 6:
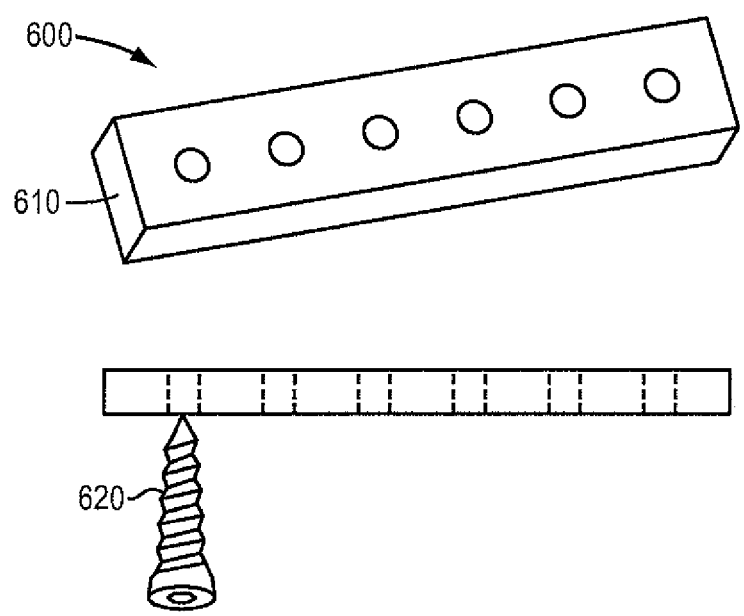
FIG. 6 is a schematic diagram of directionally solidified alloy formed into a bone fixation device, in accordance with an embodiment of the invention.

Referring to FIG. 6, in some embodiments, the bioabsorbable implant is a bone fixation device 600 for fracture fixation, e.g., a plate 610, a pin, or a screw 620.

Figure 7:
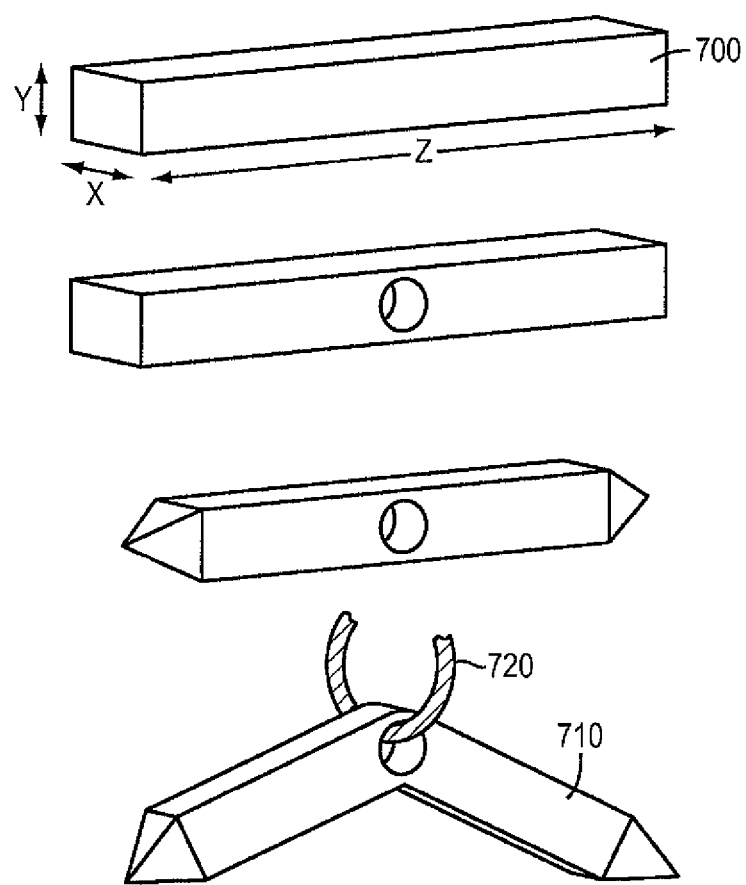
FIG. 7 is a schematic diagram of a segment of directionally solidified alloy blank formed into a bone anchor, in accordance with an embodiment of the invention.

In other embodiments, the bioabsorbable implant is a bone-to-soft-tissue fixation device, e.g., a suture anchor, an interference screw, or a cross pin. For example, referring to FIG. 7, a segment of directionally solidified formed alloy, produced as discussed above, in the form of a blank 700 may be formed into a bone anchor 710 (also referred to as a suture anchor) for soft tissue reattachment by means of a suture 720.

Several key features of the directionally solidified structures differentiate their performance from polycrystalline alloys of the same alloy composition and geometry (cross-sectional area). First, they retain strength and physical integrity longer under corrosion conditions (in vivo) due to the elimination of vulnerable grain boundaries that contain Fe and other impurities that result in mini-galvanic cells with the Mg—Li alloy. For many implant applications, maintaining strength and integrity through the early healing periods is critical for both soft and hard tissue applications.

Secondly, they inherently possess better ductility and fatigue resistance, since mechanical failure (in the absence of corrosion) is most often initiated at a micro-crack that forms at the interface of two grains under tensile or compressive load. This feature of directionally solidified alloys is currently utilized for critical load bearing non-implant applications such as turbine rotors.

Thirdly, because the loss of strength and mass is through surface corrosion and erosion, they degrade more "gracefully" in vivo, i.e. fragmentation starts later and with smaller and less injurious intermediate fragments.

In some embodiments, an implantable tissue filler such as a soft tissue filler, e.g., collagen, or a hard tissue filler, e.g., bone paste, or an augmentation implant, includes a particulate material that includes more than about 70% by weight magnesium and about 2-20% by weight lithium, with the particulate material being substantially free of rare earth metals. The paste may be a suspension of fine particles (e.g., average particle diameter ranging from 1 to 20 microns, including mixtures thereof) in a carrier of biocompatible wax or biodegradable polymer having a molecular weight of less than about 10000 Daltons. The paste may be used to seal defects created by trauma or surgical intervention in large bones, and is preferably absorbed in 3-9 months as the bone heals. The suitable Mg—Li particulate material may be sourced from ACI Alloys, based in San Jose, Calif., and a suitable biodegradable polymer, e.g., poly-co-lactide-glycolide, may be obtained from Purac Biochem, based in Gorinchem, The Netherlands.

Figure 8:
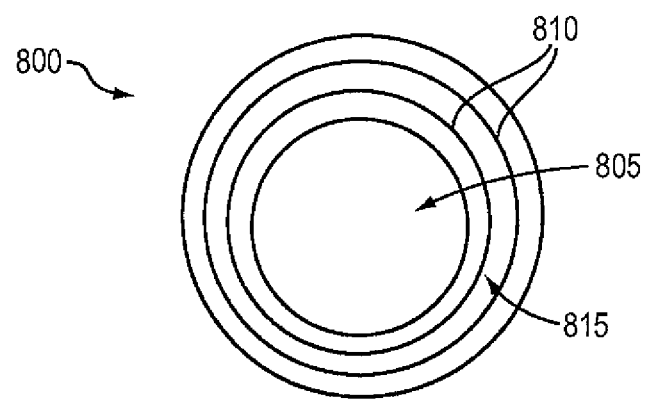
FIG. 8 is a schematic diagram illustrating a multi-layer wire formed in accordance with an embodiment of the invention.

Referring to FIG. 8, a multi-layer wire 800 may have alternating layers of magnesium alloy and high-purity Fe. The multi-layer wire may be formed by extrusion of a core wire 805 followed by deposition, such as vapor, chemical, or electro-deposition, of at least two alternating layers 110, 115 of (i) magnesium and/or a magnesium alloy and (ii) high-purity Fe and/or an Fe alloy. The magnesium alloy may be a minimum of 70% magnesium, and may include one or more elements such as Li, Zn, Ca, and/or Fe. The Fe may be, e.g., at least 99.999% pure, and the layer containing iron may have a thickness of less than about 5 microns. In some embodiments, the core may include iron with layers 810 including magnesium and layer 815 including iron. In other embodiments, the core may include magnesium with layers 810 including iron and layer 815 including magnesium.

In an exemplary process, a high purity (e.g., 99.999%) Fe wire may be formed by traditional methods of casting a rod having length of 20 cm and a diameter of 5 mm, a size suitable for conventional jewelers swaging and wire drawing machines. Multiple cycles of die-drawing and thermal annealing may be performed, until the diameter of the rod has been sufficiently reduced, e.g., to approximately 55 microns, using equipment customized for handling magnesium. The wire may then be electropolished by equipment customized for medical applications. The electropolishing removes surface contaminants from drawing and decreases surface roughness. A diameter reduction of about 5 microns is generally sufficient for removing surface contaminants and decreasing surface roughness. Accordingly, the electropolishing may reduce the diameter further to, e.g., 50 microns.

The wire may be used as the core of a multi-layer wire of 100 microns in diameter, suitable for a coronary stent strut. The Fe core may provide radio-opacity to the multi-layer wire so that it is visible by x-ray, which may be useful during the implantation procedure. The diameter of the core may range from 10 microns to 60 microns, with lower diameters exhibiting lower radio-opacity but shorter absorption time. A magnesium-4% lithium alloy may then be evaporated by arc melting in a vacuum chamber and condensed on the surface of the cooler iron wire until a deposited thickness of, e.g., 10 microns is formed, resulting in a wire diameter of, e.g., 70 microns. The arc melting may be performed in, e.g., commercially available arc melting systems manufactured by Materials Research Furnaces, Inc. A layer of iron, having a thickness of, e.g., less than a micron, may be sputtered on the surface of the wire, also in a vacuum chamber, followed by another cycle of evaporation deposition of the Mg-4% Li alloy to a thickness of, e.g., 15 microns, yielding a wire with a diameter of, e.g., 100 microns, with multi-concentric layers of magnesium and iron. The primary purpose of the iron layer is to promote corrosion locally to accelerate fragmentation and mass loss, thereby leading to shorter absorption times.

In preferred embodiments, the primary material in the multi-layer wire is the Mg—Li alloy, and only thin layers or layer portions containing iron is needed for promotion of corrosion. Thereby, the mechanical and absorption properties of the Mg—Li are regained, while corrosion is promoted where needed through the use of iron.

In alternative embodiments, a magnesium wire or any other bioabsorbable material may be used as the core, with alternating layers deposited thereover, as described above. The magnesium core multi-layer wire may provide faster absorption times than an iron core, but at lower strength and radio-opacity. In still other embodiments, a multi-layer wire may have a number of alternating layers of magnesium or magnesium alloy and iron or iron alloy. In some embodiments, the multi-layer wire includes a total of only two layers a layer of magnesium or magnesium alloy and a layer of iron or iron alloy.

The final multilayer wire may be formed into a sinusoidal wave form on a multi-slide wire forming machine and subsequently formed into a tube and welded to form bioabsorbable implant, such as an endovascular stent.

Embodiments of the Mg—Fe multilayer wire may provide improved mechanical properties and radio-opacity in comparison to a 100% or monolithic magnesium wire, and may exhibit improved or accelerated absorption time and biocompatibility in comparison to a 100% Fe monolithic wire.

Figure 9:
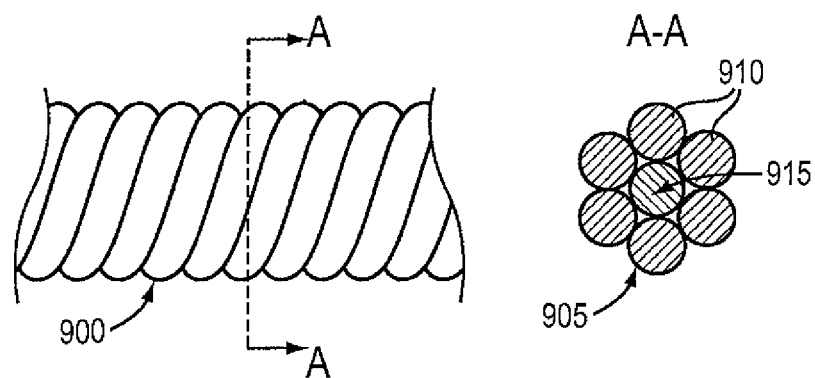
FIG. 9 is a schematic diagram illustrating a twisted composite wire formed in accordance with an embodiment of the invention.

Referring to FIG. 9, a twisted composite wire 900 may include a cylindrical sheath of three or more magnesium alloy wires 910, in intimate physical contact with a core wire of high purity Fe 915. A sheath including six magnesium alloy wires may be preferred in view of geometric packing considerations. The magnesium alloy may include a minimum of 70% magnesium, and may include one or more elements such as Li, Zn, Ca, and/or Fe.

The magnesium alloy wires may be drawn to define a preferred diameter by extrusion and subsequent die drawing and annealing cycles. For example, if a 120 micron strut is desired, a preferred diameter of the magnesium wires may be, e.g., 40 microns. A 6-strand twisted wire with a core has a diameter of three strand diameters, i.e., 120 microns. A high purity (e.g., 99.999%) Fe wire may also be formed by similar conventional wire forming methods. A diameter of the Fe wire may be the same diameter as that of the magnesium alloy wires, e.g., 40 microns. Alternatively, a 40 micron iron hollow or hypo tube wire may be used as a core wire.

A twisted composite wire can subsequently be formed by twisting the magnesium alloy wires around the single Fe wire core, with about 10 to 20 twists per cm on a fine coiling machine. Exemplary commercial sources for coiling machines include Kinefac Corp, based in Worcester Mass., and Custom Wire Technologies, based in Washington, Wis. The twisted composite wire may then be placed in a vacuum chamber and coated by evaporation with magnesium alloy to a thickness of 5 to 15 microns, enough to form a contiguous film of alloy encapsulating the individual wires together. The resulting composite wire may have a diameter of approximately 130 microns. The wire may then be formed into a planar sinusoidal waveform, wrapped on a round tool to form the planar structure into a cylinder, and resistance welded in two locations per ring to form a balloon expandable stent structure.

The size of the individual wires may be smaller or larger based on the desired final diameter of the twisted wire composite depending on the implant application. Whereas 40 micron wires may be suitable for forming a twisted structure for a coronary stent diameter of 120 microns, an application such as a bone pin with a 1 mm bone pin may require individual wires of 300 micron in diameter. Another approach to for achieving larger diameter implants may be to increase the number of sheath and core wires, for example, three individual Fe core wires may be combined with eight Mg sheath wires.

In some embodiments, a plurality of intertwined wires including Mg may define a strand. At least one of the wires may have defined on its surface an Fe-rich layer formed by, e.g., vapor, chemical, and/or electro-deposition.

The iron-containing composite wire and the multilayer wire described possess higher strength, greater radio-opacity, and accelerated fragmentation in comparison to a conventional magnesium alloy alone.

EXAMPLES

Example 1

A high purity alloy of Mg-4% Li may be melted under vacuum and cast into a graphite mold resulting in a rod of 25 mm diameter by 40 cm long. The rod is subsequently drawn into a wire of 100 microns in diameter by conventional die drawing and annealing methods. The wire possesses an elongation-at-break percentage greater than 20%. This material property indicates the percentage increase in length that is attained before the material breaks under tension. The wire may then be formed on a four-slide machine into a continuous sinusoidal geometry with periodic straight segments. The continuous wire form may then be wrapped around a 3.0 mm diameter mandrel allowing contact between adjacent rings, and capacitive discharge welded in selective locations to form a flexible cylindrical intraluminal stent. The stent may be spray coated with a formulation of 50% D,L-PLA absorbable polymer and 50% Sirolimus with a drug loading of approximately 10 micrograms per mm of stent length. The coated stent is crimped on the balloon of an angioplasty catheter, sterilized by Ethylene Oxide gas, and packaged in a foil package backfilled with nitrogen gas. The stent provides acute scaffolding of the vessel but is fully absorbed in 6 months post implantation.

Example 2

A high purity alloy of 87.5% magnesium and 12.5% lithium (by weight) may be vacuum melted and cast under a protective atmosphere and into a 20 mm diameter rod. The rod may be subsequently reprocessed by equal channel angular pressing ("ECAP") to form an ultra-fine microstructure with a grain size of less than 1 mm. The rod may be die drawn into a 100 micron diameter wire by conventional methods of sequential drawing and annealing. The wire may be formed into a sinusoidal waveform of 1 mm amplitude with periodic straight segments at ring intervals, wrapped on a cylindrical mandrel, and resistance welded in discrete locations to form an expandable metal tube. The entire assembly may be coated with a formulation of approximately 6% PTx in 90-10 PLGA, crimped on an angioplasty catheter, packaged and sterilized.

Example 3

A high purity alloy of 91.5% magnesium and 7.5% lithium (by weight) and 1% Zn may be vacuum melted and cast into a sheet mold equipped with an ultrasonic transducer resulting in a fine grain alloy (less than 5 micron average grain size). The sheet may be rolled down to a thickness of 100 microns, and then divided into square (100 micron×100 micron) continuous wires. The square wire may be formed on a wire form machine into a continuous undulating structure which is capable of being spirally wrapped on a cylindrical mandrel. The helical wire structure may then be inserted into a precision steel cavity mold and liquid 85-15 PLGA polymer may be injected to form longitudinal connectors that transform the structure into an integral tubular structure. The entire assembly may be coated with a formulation of approximately 50% Sirolimus and 50% D,L-PLA with a total dose of about 10 microgram per mm of stent length. The resulting absorbable DES may be crimped on an angioplasty catheter, packaged and sterilized.

Example 4

A high purity alloy of 87.5% magnesium and 12.5% lithium (by weight) may be vacuum melted and cast under a protective atmosphere and into a 20 mm diameter rod. The rod may subsequently be reprocessed by ECAP to form an ultra-fine microstructure with a grain size of less than 1 mm. The rod may be center drilled to form a cylinder and then drawn by conventional methods to form a hypo tube of 125 microns wall thickness and outside diameter of 2.0 mm. The tube may be laser machined to form a mesh that is capable of expansion by a balloon catheter to 4.0 mm in diameter without cracking. The laser cut mesh tube may be electropolished so that the average thickness is reduced to 115 microns, and anodized to form a protective oxide layer. The entire assembly may be coated with a formulation of approximately 8% PTx in D,L-PLA resulting in a dose of about 0.5 microgram per mm of stent, then crimped on an angioplasty balloon catheter, packaged and sterilized.

Example 5

An in vivo study was performed with Mg—Li (3.5% by weight) wire, having a diameter of 125 microns, in a rat carotid artery peri-adventitia model. Histological analysis confirmed very low inflammation at the site of implantation at 7, 28 and 90 days follow-up. Whereas magnesium alloys that have been used in human clinical trials may take 9 months to 2 years to absorb, the Mg—Li alloy surprisingly was largely absorbed by the 90 day follow-up time point by both histology and SEM analysis. It should be noted that full absorption within 6 months has significant value, since patients are preferably kept on antiplatelet therapy for 6 months or shorter. Because of the high solubility of the salts that form during degradation, the stent struts described herein can be absorbed safely and quickly, whereas the alloys that have been used in human clinical trials form insoluble salts of heavy metals that can take from 2 years to potentially never to be absorbed from the site.

Example 6

A high purity alloy of magnesium-8.5% lithium by weight may be cast into a 12 mm rod, drilled, and subsequently drawn into a hypo tube of approximately 2.5 mm in diameter. The tube may be laser cut and electropolished to form a stent with a strut thickness of 90 microns. The stent may be coated with a formulation of 75-25 PLGA with 6% Paclitaxel with a total loading of about 1 microgram of drug per mm stent length. The stent may be crimped on an angioplasty balloon catheter, packaged and sterilized. When implanted, the stent preferably retains mechanical integrity for a minimum of 2 weeks, after which it may be rapidly absorbed by the local tissue with minimal inflammation and no evidence of toxicity.

Example 7

A composite twisted wire structure may be made of six strands of high purity Mg-2% Ca wire twisted around a center core of 99.99% pure Fe wire. Both the Mg and Fe wire diameters may be 0.4 mm, yielding a twisted structure with a diameter of approximately 1.25 mm. The twisted assembly may be cut to 24 inch lengths, packaged, and sterilized. The wire may be used for sternum closure for pediatric patients following open thoracic surgery such as open heart surgery, where the absorbable device would eliminate longer term complications relating to normal growth with age that conventional stainless steel implants pose.

Example 8

A 1.0 mm square wire of Mg-4% Li may be processed with an ultimate elongation of greater than 20%. The square wire may then cut to 16 mm long, and formed into an open "V" shape for loading into a clip applier (Ethicon Inc., Somerville N.J.). The clip may be used in vasectomy procedures to ligate the vasa deferentia for reproductive sterilization. After the lumen of the vessel heals in a collapsed or closed state, the clip fragments and is absorbed at the site within 90 days, preventing long term complications such as inflammation at the site that can impact sexual health.

While an exemplary embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

Those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described. Various materials, geometries, sizes, and interrelationships of elements may be practiced in various combinations and permutations, and all such variants and equivalents are to be considered part of the invention.

What is claimed is:
1. A bioabsorbable implant, comprising:
an elongated core portion; and
an outer portion disposed on and surrounding the elongated core portion, the outer portion comprising magnesium;
wherein the elongated core portion and outer portion define at least part of the bioabsorbable implant,
wherein the elongated core portion has a different composition than the outer portion, and
wherein the outer portion comprises a cylindrical sheath surrounding the elongated core.
2. The bioabsorbable implant of claim 1, wherein the outer portion comprises at least 70% by weight magnesium, and about 2-20% by weight lithium.
3. The bioabsorbable implant of claim 1, wherein the outer portion comprises at least two layers of alternating compositions selected from the group consisting of magnesium, iron, and alloys thereof disposed on the core portion.
4. The bioabsorbable implant of claim 3, wherein each of the at least two layers is formed by at least one of vapor, chemical, and electro-deposition.
5. The bioabsorbable implant of claim 3, wherein a thickness of a layer comprising iron is less than about 5 microns.
6. The bioabsorbable implant of claim 1, wherein the outer portion comprises at least three wires comprising magnesium and wherein the cylindrical sheath is in intimate contact with the elongated core portion.
7. The bioabsorbable implant of claim 6, wherein the at least three wires are spirally twisted about the core portion.
8. The bioabsorbable implant of claim 6, wherein the outer portion comprises a plurality of intertwined wires comprising magnesium and defining a strand.
9. The bioabsorbable implant of claim 8, wherein an iron-rich layer formed by at least one of vapor, chemical, and electro-deposition is defined on a surface of at least one of the wires.
10. The bioabsorbable implant of claim 8, wherein the outer portion is a six-strand twisted wire.
11. The bioabsorbable implant of claim 6, wherein the elongated core portion comprises at least one core wire, and wherein the sheath comprises 10 to 20 wire twists per lengthwise centimeter of the at least one core wire.
12. The bioabsorbable implant of claim 6, wherein the sheath comprises at least six wires comprising magnesium.
13. The bioabsorbable implant of claim 6, wherein the at least three wires comprise a magnesium-alloy coating having a thickness between 5 and 15 microns.
14. The bioabsorbable implant of claim 6, wherein the elongated core portion comprises at least one wire, and wherein the implant is a bioabsorbable coronary stent.
15. The bioabsorbable implant of claim 1, wherein the elongated core portion comprises at least one core wire comprising iron.
16. The bioabsorbable implant of claim 1, wherein the implant is a bioabsorbable coronary stent.
17. The bioabsorbable implant of claim 1, wherein:
the core portion comprises an elongated core wire; and
the sheath comprises at least three wires twisted around the core wire, each of the three wires comprising at least 70% magnesium by weight.
18. The bioabsorbable implant of claim 17, wherein each of the three wires comprises no more than about 20% lithium by weight.
19. The bioabsorbable implant of claim 17, wherein the core wire has a core diameter, and each of the at least three twisted wires has a wire diameter, and wherein the core diameter is substantially the same as the wire diameter.

20. The bioabsorbable implant of claim 17, wherein the implant is a bioabsorbable coronary stent.

21. The bioabsorbable implant of claim 1, wherein the outer portion comprises at least six magnesium-alloy wires spirally twisted about, and in direct contact with, the elongated core portion, wherein the six wires comprise at least 70% magnesium by weight.

22. The bioabsorbable implant of claim 21, wherein each of the six magnesium-alloy wires further comprises about 2-20% by weight lithium.

23. The bioabsorbable implant of claim 22, wherein each of the six magnesium-alloy wires is substantially free of rare earth metals.

24. The bioabsorbable implant of claim 21, wherein the elongated core portion comprises a plurality of core wires.

25. The bioabsorbable implant of claim 24, wherein the at least six wires form the sheath surrounding the plurality of core wires.

26. The bioabsorbable implant of claim 25, wherein the sheath comprises eight magnesium-alloy wires twisted about the plurality of core wires.

27. The bioabsorbable implant of claim 21, wherein the elongated core portion comprises a hollow tube wire.

28. The bioabsorbable implant of claim 1, wherein the implant is a bioabsorbable coronary stent, wherein the elongated core portion comprises at least one core wire, and wherein the outer portion comprises:
   at least three intertwined wires defining the cylindrical sheath which is in intimate contact with the elongated core portion, wherein the at least three wires are spirally twisted about the core portion, with 10 to 20 wire twists per lengthwise centimeter of the at least one core wire; and
   at least 70% by weight magnesium, and about 2-20% by weight lithium, wherein each of the at least three intertwined wires is substantially free of rare earth metals.

29. The bioabsorbable implant of claim 28, wherein the at least three wires comprise a magnesium-alloy coating having a thickness between 5 and 15 microns.

* * * * *